United States Patent [19]

Insel et al.

[11] Patent Number: 4,689,299

[45] Date of Patent: Aug. 25, 1987

[54] HUMAN MONOCLONAL ANTIBODIES AGAINST BACTERIAL TOXINS

[75] Inventors: Richard A. Insel, Rochester, N.Y.; Francis Gigliotti, Memphis, Tenn.

[73] Assignee: University of Rochester, Rochester, N.Y.

[21] Appl. No.: 534,658

[22] Filed: Sep. 22, 1983

Related U.S. Application Data

[63] Continuation-in-part of Ser. No. 428,747, Sep. 30, 1982, abandoned.

[51] Int. Cl.$^4$ .................... C12N 5/00; C12N 15/00
[52] U.S. Cl. ..................... 435/240.27; 435/172.2; 935/95; 935/96; 424/92; 530/387
[58] Field of Search .................... 435/172.2, 240, 241, 435/172.2; 424/85, 87; 260/112 R, 112 B; 935/95, 96

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 424/85 |
| 4,271,145 | 6/1981 | Wands et al. | 424/85 |
| 4,349,528 | 9/1982 | Koprowski et al. | 424/85 |
| 4,529,694 | 7/1985 | Lazarus et al. | 435/240 |

FOREIGN PATENT DOCUMENTS

| | | |
|---|---|---|
| 82/1461 | 5/1982 | PCT Int'l Appl. . |
| 84/04458 | 11/1984 | PCT Int'l Appl. . |
| 2021262 | 11/1979 | United Kingdom . |
| 2086937 | 5/1982 | United Kingdom . |

OTHER PUBLICATIONS

Kozbor et al., J. Immunol., vol. 127, pp. 1275–1280, 1981.
Kozbor et al., Hybridoma, vol. 1, pp. 323–328, 1982.
Remmers, E. F., et al., Infection and Immunity, vol. 37, pp. 70–76, 1982.
Kozbor et al, 1982, Proc. Nat'l Acad. Sci. U.S.A. 79:6651–6655.
G. Kohler and C. Milstein, Nature, 256:495–497 (1975).
G. Kohler and C. Milstein, Eur. J. Immunol., 6:511–519 (1976).
D. E. Yelton and M. D. Scharff, Ann. Rev. Biochem., 50:657–680 (1981).
V. R. Zurawski, et al., Fed. Proc. 39(3):1204, Abstract 4992, 64th Annual Meeting of the Fed. Am. Soc. Exp. Biol., Apr. 13–18, 1980, Anaheim, CA (1980).
V. R. Zurawski, et al., Science, 199:1439–1441 (1978).
V. R. Zurawski, et al., Clin. Res., 26(3):558A (1978).
V. R. Zurawski, et al., in: Current Topics in Microbiology and Immunology, vol. 81 (F. Melchers, M. Potter and N. L. Warner, eds.), Springer-Verlag, Berlin, pp. 152–155 (1978).
V. R. Zurawski, et al., Abstracts of the 13th International Leucocyte Culture Conference, Ottawa, Canada, p. 98 (1979).
V. R. Zurawski, et al., in: Monoclonal Antibodies (R. Kennett, T. McKearn, and K. Bechtol, eds.), Plenum Press, New York, pp. 19–33 (1980).
D. Kozbor and J. C. Roden, J. Immunol., 127(4):1275–1280 (1981).
R. Nowinskie et al., Science, 210:537–539 (1980).
J. Schlom et al., Proc. Natl. Acad. Sci. USA, 77(11):6841–6845 (1980).
R. Levy and J. Dilley, Proc. Natl. Acad. Sci. USA, 75(5):2411–2415 (1978).
S. Brown et al., J. Immunol., 125(3):1037–1043 (1980).
L. Olsson and H. S. Kaplan, Proc. Natl. Acad. Sci. USA, 77(9):5429–5431 (1980).
C. M. Croce et al., Nature, 288:488–489 (1980).
M. Pollack and L. S. Young, J. Clin. Invest., 63:276–286 (1979).

Primary Examiner—Blondel Hazel
Attorney, Agent, or Firm—Pennie & Edmonds

[57] ABSTRACT

The production of stable hybrid cell lines that secrete human monoclonal antibodies against bacterial toxins by fusing post-immunization human peripheral blood lymphocytes with nonsecretor mouse myeloma cells is described. Using the method, protective monoclonal antibodies against tetanus toxin and diphtheria toxin were produced that bind tetanus toxin and diphtheria toxin in vitro, respectively, and prevent tetanus and diphtheria in vivo in animals, respectively.

10 Claims, No Drawings

HUMAN MONOCLONAL ANTIBODIES AGAINST BACTERIAL TOXINS

This application is a continuation-in-part of application Ser. No. 428,747, filed Sept. 30, 1982, now abandoned.

TABLE OF CONTENTS

1. Introduction
2. Background of the Invention
   2.1. Monoclonal Antibodies
      2.1.1. Rationale for Use of Monoclonal Antibodies
      2.1.2. Human Monoclonal Antibodies
      2.1.3. Application to Infectious Disease
         2.1.3.1. Prevention and Therapy of Infections
         2.1.3.2. Vaccine Development
         2.1.3.3. Diagnosis
      2.1.4. Human Administration of Monoclonal Antibodies
   2.2. Tetanus
      2.2.1. Tetanus Toxin
      2.2.2. The Disease
      2.2.3. Approaches to Prevention and Therapy
   2.3. Diphtheria
      2.3.1. Diphtheria Toxin
      2.3.2. The Disease
      2.3.3. Approaches to Prevention and Therapy
3. Summary of the Invention
4. Description of the Invention
   4.1. The Antigen
   4.2. Somatic Cells
   4.3. Myeloma Cells
   4.4. Fusion
   4.5. Isolation of Clones and Antibody Detection
   4.6. Uses for Bacterial-Toxin Specific Human Monoclonal Antibodies
5. Examples
   5.1. Construction of Hybridomas Secreting Antibodies to Tetanus Toxin and Diphtheria Toxin
      5.1.1. Immunization with Toxoid
      5.1.2. Isolation of Mononuclear Cells
      5.1.3. Enrichment for B Lymphocytes
      5.1.4. Fusion Procedure for Hybrid Formation
      5.1.5. Screening for Antibody-Producing Hybrids
      5.1.6. Cloning of Anti-Tetanus Toxin and Anti-Diphtheria Toxin Antibody-Producing Hybrids
   5.2. Characterization of Hybrid Clones
   5.3. Determination of Anti-Tetanus Toxin Monoclonal Antibody Specificity
      5.3.1. Iodination of Tetanus Toxin
      5.3.2. Papain Cleavage of the Toxin
      5.3.3. Precipitation of Toxin Fragment-Antibody Complexes
      5.3.4. Identification of Antibody Specificity
   5.4. Determination of Biological Activity of Monoclonal Antibody Produced

1. INTRODUCTION

This invention relates to the production of and applications for antibodies specific for bacterial toxins and, in particular, for tetanus toxin and diphtheria toxin. This invention further relates to the production of human monoclonal antibodies against bacterial toxins by fused cell hybrids. A bacterial toxin may be defined as a chemical substance produced by bacteria that damages the host if it reaches susceptible tissues. Tetanus is an nfectious disease caused by the neurotoxin of *Clostridium tetani* which poses a serious health problem worldwide despite efforts to control the disease through pre-infection immunization programs. Diphtheria is an infectious disease caused by the exotoxin of lysogenic strains of *Corynebacterium diphtheriae*. While this disease is controlled in countries such as the U.S. where mass immunization of the population is practiced, it still poses a health threat in those countries where immunization programs are rare. The anti-tetanus toxin and anti-diphtheria toxin human monoclonal antibodies of the present invention can neutralize tetanus toxin and diphtheria toxin, respectively. They can prevent tetanus and diphtheria disease, and hence represent new chemotherapeutic agents for the prevention and/or treatment of toxin-induced diseases.

The invention provides a method for fusing post-immunization human peripheral blood lymphocytes with non-secretor mouse myeloma cells to produce stable fused cell hybrids secreting human antibodies against bacterial toxins. Once cloned, these cell lines can be maintained continuously to produce an unlimited homogeneous monoclonal antibody population that can be isolated and used clinically for diagnosis, immunoprophylaxis and immunotherapy, for production and purification of vaccines, as well as for other research purposes.

2. BACKGROUND OF THE INVENTION

2.1. Monoclonal Antibodies

Köhler and Milstein demonstrated in 1975 that antibody-producing cell lines could be produced by somatic cell hybridization, a process by which lymphocytes and myelomas are fused into single cells and cloned [G. Köhler and C. Milstein, Nature 256:495–497 (1975)]. The resulting cell lines, termed "hybridomas", retain the antibody-secreting capacity of the parental lymphocyte and, at the same time, gain the immortality of the parental myeloma cell line, that is, the ability to reproduce themselves indefinitely. With this combination of features, hybridomas produce unlimited homogeneous antibody (monoclonal antibody) that can be selected for desired specifically and biologic activity. Monoclonal antibodies are replacing conventional antisera in diagnostic laboratories and are providing new insights in medicine [R. H. Kennett, T. J. McKearn and K. B. Bechtol (editors), Monoclonal antibodies, Plenum Press, New York (1980); D. E. Yelton and M. D. Scharff, Ann. Rev. Biochem. 50:657–680 (1981); and M. S. Mitchell and H. F. Oettgen (editors), Hybridomas in the diagnosis and treatment of cancer, Progress in cancer research and therapy, Vol. 21, Raven Press, (1982)]. Monoclonal antibodies produced by hybrid cell lines have potential use in many areas of medicine including therapy of human infection, malignancy, and transplantation rejection.

2.1.1. Rationale for use of Monoclonal Antibodies

An animal immunized with a foreign substance, or antigen, responds by producing antibodies, immunoglobulins with specificity for the immunogen. The post-immunization antiserum contains antibodies of varying isotype (IgG, IgM, or IgA), affinity, and biological activity (opsonic, lytic or agglutinating activity). In addition, conventional antiserum is composed of a complex polyclonal mixture of antibodies directed to different antigenic determinants of the immunogen. If the antigen is a protein, for example, an antigenic determinant may be one of the many peptide sequences [generally 6-7 amino acids in length (M. Z. Atassi, Molec. Cell. Biochem. 32:21-43 (1980)] that make up the entire protein molecule. Each individual antigenic determinant, or epitope, stimulates clones of B lymphocytes to proliferate and differentiate to become plasma cells that produce a single type of antibody. B lymphocyte clones may respond to only minor determinants, or even contaminants, in the preparation. Thus, the resulting antiserum reflects the contribution of multiple antibody-secreting clones that contribute both desired and undesired antibodies. These undesirable antibodies must then be adsorbed from the antiserum to prevent interference with its intended use. Conventional antisera is difficult to reproduce because individual animals respond unpredictably with varying proportions of antibody of different activity and specificity; therefore, supplies are often limited.

For years immunologists have sought techniques to induce antibodies with restricted specificities for use in studying and manipulating the immune response and for use as diagnostic and therapeutic reagents. One approach to prepare restricted antibodies has been to use highly purified antigens as immunogens. Hybridoma antibody technology provides an approach to production of a single restricted antibody type that has the distinct advantage of allowing the use of complex unpurified antigens for the production of virtually unlimited amounts of identical antibody to a single antigen of the mixture. It should be noted that monoclonal antibodies raised against a single antigen may be distinct from each other depending on the determinant that induced their formation; but for any given hybridoma (clone), all of the antibodies it produces are identical.

The concept behind monoclonal antibody production is relatively simple, although successful production thereof remained elusive until 1975. Once the DNA of a B cell has been committed to form antibody with a given Ig class and specificity, all subsequent antibodies produced by the B cell or its progeny will be identical. Therefore, immunologists sought to develop a technique enabling single antibody-secreting cells to grow continuously in culture in order to produce homogeneous antibody. Multiple myeloma is a neoplastic proliferation of a single clone of plasma cells producing a single homogeneous antibody. However, with some exceptions [M. Seligmann and J. C. Brouet, Seminars in Hematology 10:163-177 (1973)], the antigenic specificity of these naturally-occurring monoclonal antibodies is unknown. These tumor cells (plasmacytomas) of both murine and human origin have been adapted to grow in continuous cell culture. Höhler and Milstein demostrated that hybrids produced after fusing cultured murine plasmacytoma cells with spleen cells of a mouse recently immunized with sheep erythrocytes could secrete large amounts of homogeneous antibody to sheep erythrocytes and grow continuously in culture [G. Köhler and C. Milstein, Nature 256:495-497 (1975); and G. Köhler and C. Milstein, Eur. J. Immunol. 6:511-9 (1976)]. They demonstrated that a single spleen cell committed to production of antibody to sheep erythrocytes had fused its cell membrane with that of a myeloma cell to produce a single cell hybrid-myeloma or "hybridoma". The single B-cell donor had provided the genetic information for production of only one type of heavy and light chain and the tumor cell had provided the genetic information for immortalization of the hybridoma. Thus, a single antibody specificity and isotype (monoclonal) was produced continuously in vitro. Because fusion of a whole spleen cell suspension with myeloma cells generates hybrids producing a multitude of different antibodies with both desired and undesired specificity, single clones producing the desired antibody must be identified, isolated, and grown. Since the early experiments, refinements have been introduced that allow rapid selection of single clones producing the desired antibody [R. H. Kennett, T. J. McKearn and K. B. Bechtol (editors), Monoclonal antibodies, Plenum Press, New York (1980); and F. Melchers, M. Potter and N. Warner (editors), Lymphocyte hybridomas. Curr. Top. Microbiol. and Immunol., Springer-Verlag, Berlin 81:1-246 (1978)]. Monoclonal methods have been used to produce antibodies to antigens other than the sheep red blood cells of Köhler and Milstein. For instance, it has been reported that monoclonal antibodies have been raised against tumor cells [U.S. Pat. No. 4,172,124] and viruses [U.S. Pat. No. 4,196,265 and U.S. Pat. No. 4,271,145]. It has also been reported that murine monoclonal antibodies have been produced against tetanus toxin and that these antibodies exhibit protective biological activity in animals. [V. R. Zurawski, et al., Fed. Proc. 39(3): Abstract 4922, 64th Annual Meeting of the Fed. Am. Soc. Exp. Biol., Apr. 3-18, 1980, Anaheim, CA (1980)]. The use of hybridoma technology to produce unlimited amounts of standardized, homogeneous antibodies effectively means that antibodies can be considered a new class of chemical reagents.

2.1.2. HUMAN MONOCLONAL ANTIBODIES

Most monoclonal antibodies have been produced through the fusion of mouse or rat spleen cells with murine plasmacytoma lines. These monoclonal antibodies are potentially unsuitable for in vivo human use due to the risk of adverse reaction to proteins of murine origin. Routine employment of monoclonal antibodies in vivo in the diagnosis and therapy of human disease while avoiding sensitization to foreign proteins potentially requires production of human monoclonal antibodies. Three approaches have been employed to produce human monoclonal antibodies. In the first, human lymphocytes are fused with murine myeloma cells [R. Levy and J. Dilley, Proc. Natl. Acad. Sci. USA 77:2411-15 (1978)]. Although interspecies fusions tend to rapidly lose human donor chromosomes, human antibodies to the Forssman antigen (a glycolipid constituent of the influenza virion) [Nowinski et al., Science 210:537-539 (1980)] and to mammary carcinoma cells [J. Schlom et al., Proc. Natl. Acad. Sci. USA 77:6841-45 (1980)] have been produced by fusing murine plasmacytomas with human lymphocytes. It is noteworthy that Zurawski et al. [Continuously proliferating human cell lines synthesizing antibody of predetermined specificity, in: R. Kennet, T. McKearn and K. Bechtol (editors), Monoclonal antibodies, p. 25, Plenum Press, New York (1980)] have reported an unsuccessful attempt to obtain anti-tetanus toxoid antibody-producing hybridomas. These investigators took peripheral blood cells from humans immunized with tetanus toxoid, transformed the cells in vitro with Epstein-Barr virus (EBV), and fused the EBV-transformed cell lines with murine myelomas. None of the resulting hybrids produced human antibody against tetanus toxoid.

Development of human myeloma cell lines deficient in hypoxanthine phosphoribosyltransferase (HPRT) for use as fusion partners for human lymphocytes has provided a second approach. Recently, several human myeloma and lymphoblastoid cell lines have been used for fusions with human spleen cells or peripheral blood lymphocytes. Hybrids producing humn antibody to 2,4-dinitrophenol [L. Olsson and H. S. Kaplan, Proc. Natl. Acad. Sci. USA 77:5429–5431 (1980); and PCT International Application Number PCT/US81/00957 filed July 15, 1981 in the names of H. S. Kaplan and L. Olssen] and to measles virus [C. M. Croce et al., Nature 288:488–89 (1980); and U.K. Application No. GB2086937, published March 1, 1982] have been reported. However, fusions using some of the cell lines employed have had only limited success. The ideal myeloma cell line for the production of human monoclonal antibody has yet to be developed, although several new human myeloma lines are actively being investigated.

The third approach to the production of human monoclonal antibodies does not involve hybridoma technology. Instead of fusing lymphocytes and myeloma cells by somatic cell hybridization techniques, some investigators have infected antigen-stimulated B-cells in vitro with B-cell-specific viruses in an attempt to induce the formation of continuous, or transformed, cell lines capable of synthesizing specific antibodies [D. E. Yelton and M. D. Scharff, Amer. Scientist 68: 510–516 (1980)]. For instance, Zurawski et al. [Science 199:1439 (1978)] infected the peripheral blood mononuclear cells of individuals recently immunized against tetanus toxoid with EBV in vitro. Several of the resulting transformed lymphoblastoid cultures produced tetanus-specific antibody. However, there was a major drawback inherent in this technique. None of the antibody producing cell lines obtained could be cultured continously, either because they became overgrown by competing cells, had chromosome alterations and/or lost differentiated function due to changes in regulatory mechanisms. It is applicants' belief that prior to this invention, no one has established a stable cell line (either transformed human ymphoblastoid or hybridoma) capable of synthesizing tetanus toxin-specific or diphtheria toxin-specific human monoclonal antibodies, particularly human monoclonal antibodies with protective biologic activity in animals.

2.1.3. Application to Infectious Disease

2.1.3.1. Prevention and Therapy of Infections

Passive antibody therapy is used to prevent several childhood infections [E. R. Stiehm, Pediatrics 63:301–319 (1979)]. There is the prospect that human monoclonal antibodies may be able to replace high-titered human immunoglobulins. In addition, this approach may prove especially important for production of antibody for passive immunization for treatment of infections incompletely controlled by antibiotics and/or for which no readily available immunoglobulin preparation currently exists. The use of passive antibody to prevent and/or treat gram negative sepsis and shock, Pseudomonas infection, and group B streptococcal infection is being experimentally investigated [E. J. Ziegler et al., Trans. Assoc. Am. Physicians 91:253–258 (1978); M. Pollack and L. S. Young, J. Clin. Invest. 63:278–286 (1979); and L. C. Vogel et al., Ped. Res. 14:788–792 (1980)]. Recently, monoclonal antibodies have been shown to be protective against infection from *Haemophilus influenzae* b, and *Streptococcus pneumoniae* and have been shown to be effective in treatment of experimental *H. influenzae* b bacteremia [F. Gigliotti and R. Insel, J. Inf. Dis. 146:249–254 (1982); and D. E. Briles et al., J. Exp. Med. 153:694–705 (1981)]. Antibodies were shown to be therapeutic for certain infections prior to the antibiotic era [H. E. Alexander et al., J. Pediatr. 20:673–698 (1942). With the advent of the development of monoclonal antibodies safe for human use, the concept of using antibodies as an adjunct to antibiotics to lower morbidity and mortality rates of certain infections may be reexplored.

2.1.3.2. Vaccine Development

The use of monoclonal antibodies to define protective antigens of microorganisms and to purify these antigens should aid in producing new and improving old vaccines. This approach is being exploited in evaluating outer membrane proteins as candidate vaccines for prevention of *Haemophilus influenzae* b [E. J. Hansen et al., Lancet 1:366–368 (1982).

Monoclonal antibodies are proving useful in studying epidemiology of parasitic infections as well as in defining and purifying protective antigens of parasites that could be used as vaccines. Hybridoma antibodies to certain stages of malaria have been shown to be protective against infection and are now being used to purify individual peptides to produce vaccines [A. A. Holder and R. R. Freeman, Nature 294:361–364 (1981); and N. Yoshida et al., Science, 207:71–73 (1980)].

2.1.3.3. Diagnosis

Monoclonal antibodies are being applied to the diagnosis and to the study of the pathogenesis and epidemiology of infectious diseases. The rapid diagnosis of childhood infections, for instance, has been shown to aid in making clinical decisions regarding the initial selection of antibiotics, necessity for antibiotic prophylaxis of contacts, isolation of patients, and the necessity and duration of hospitalization [S. L. Kaplan and R. D. Feigin, Ped. Clin. N. Amer. 27:783–803 (1980); and A. J. Nahmias and C. B. Hall, Hospital Practice 49–61(1981)]. Many rapid diagnostic assays employ antibodies to detect antigens of the infecting microorganism immunologically. These antibodies, which are prepared through conventional techniques, may exhibit cross-reactivity with other microorganisms, may be of low-titer, and are of limited supply. Furthermore, certain bacterial antigens, such as the capsular polysaccharide of group B meningococcus, are poorly immunogenic. Monoclonal antibodies have the inherent capacity to obviate these deficiencies. Sensitive and specific reagents directed to even weak immunogens can be produced with hybridomas. At this time monoclonal antibodies have been used for the diagnosis of group B streptococcal infection, hepatitis, and respiratory syncytial virus and other antibodies have been produced that should be easily applied to diagnose some of the more common causes of childhood sepsis and meningitis [R. A. Polin and R. Kennett, J. Pediatr. 97:540–544 (1980); J. R. Wands et al., Lancet, I:977–980 (1982); and M. R. Tam et al., Infect. Immun. 36:1042–1053 (1982)]. Radioimmunoassays are used for serology to determine immunity to several microorganisms and antibodies are used to subtype microorganisms. Monoclonal antibodies may provide reagents that can be used to standardize and perform these assays.

The specificity of monoclonal antibodies has allowed identification of differences in viral strains that were not previously appreciated. Monoclonal antibodies to influenza, rabies, and measles viruses have been used to study the epidemiology of these infections [W. Gerhard et al., Nature 290:713–716 (1981); T. J. Wiktor and H. Koprowski, Proc. Nat. Acad. Sci. USA, 75:3938–42 (1978); and M. J. Birrer et al., Nature 293:67–69 (1981)]. The ability of the influenza hemagglutinin antigen, and to a lesser extent the neuraminidase antigen, to antigenically mutate is thought to produce new viral strains to which humans lack immunity. Pandemics of influenza infection occur with major antigen changes. With the use of monoclonal antibodies to the influenza hemagglutinin, it has been possible to detect single amino acid substitutions, classify substrains of virus, create genetic drift in vitro and study the epidemiology and mechanism of antigenic drift [W. Gerhard et al., Nature 290:713–716 (1981); and W. Gerhard and R. G. Webster, J. Exp. Med. 148:383–392 (1978)]. The differences in viral strains were not previously detectable with available antisera. The clinical observation that rabies virus vaccine may fail in some instances to provide protection against wild virus is now partially explained by the demonstration with monoclonal antibodies of antigenic differences of strains of rabies virus [T. J. Wiktor and H. Koprowski, Proc. Nat. Acad. Sci. USA, 75:3938–42 (1978)]. Measles virus is also being studied with monoclonal antibodies to explain the persistence of the virus in subacute sclerosing panencephalitis [M. J. Birrer et al., Nature 293:67–69 (1981); and K. W. Rammohan et al., Nature 290:588–589 (1981)].

Improved diagnostic assays for parasitic infection that employ hybridoma antibodies have been developed and are being applied to diagnosis in the field [D. M. Pratt and J. R. David, Nature 291:581–583 (1981); and G. F. Mitchell et al., Proc. Natl. Acad. Sci. USA 78:3165–3169 (1981)]. The complex genetic and antigenic changes of trypanosomes and the surface antigenic changes of strains of malaria at different stages in the life cycle can be exquisitely delineated with monoclonal antibodies as compared to conventional antisera.

2.1.4. Human Administration of Monoclonal Antibodies

At this time, human monoclonal antibody has not been administered to humans, but murine monoclonal antibodies have been empolyed on a limited basis for human disease. Murine monoclonal antibody to QKT3 antigen, a differentiation antigen expressed on all normal peripheral blood T lymphocytes, has been infused into patients with allogeneic kidney grafts to abort acute kidney-graft rejection by decreasing the number of circulating cytotoxic T cells [A. B. Cosimi et al., N. Engl. J. Med. 305:308–314 (1981)]. Murine monoclonal antibody with specificity for human T lymphocytes has also been administered in vivo to bone marrow transplant recipients in conjunction with in vitro monoclonal antibody treatment of the donor bone marrow to attempt to decrease the incidence and severity of acute graft-versus-host disease.

Neoplasms have been treated by administration of murine monoclonal antibody to tumor-associated antigens [J. Ritz and S. F. Schlossman, Blood 59:1–11 (1982)]. Murine monoclonal antibodies to T-cell and B-cell differentiation antigens have been used to treat adult T-cell leukemia, cutaneous T-cell lymphoma and B-cell non-Hodgkin's lymphoma [L. M. Nadler et al., Cancer Research 40:3147–3154 (1980); R. A. Miller et al., Blood 58:78–86 (1981); and R. A. Miller and R. Levy, Lancet II:226–230 (1981)].

Sensitization to murine proteins has been observed in most studies [A. B. Cosimi et al., N. Engl. J. Med. 305:308–314 (1981) and R. A. Miller et al., Blood 58:78–86 (1981)]after in vivo administration of murine monoclonal antibody. The safety, in addition to the efficacy, of murine monoclonal antibody in man requires further investigation prior to use in patients without life-threatening disease because of the risk of sensitization to foreign proteins. The use of human monoclonal antibodies can overcome the inherent drawbacks of their murine counterparts. Nevertheless, as a practical matter, careful purification of human immunoglobulins secreted by mouse-human hybrids would still be necessary prior to any possible therapeutic trials so as to remove any other contaminating mouse proteins. These proteins could be present in the tissue culture supernatant either through specific secretion by the hybrid cell or because of cell breakdown with subsequent release of cytoplasmic contents. In addition murine retrovirus particles have been found in several murine myeloma or plasmacytoma cell lines [C. M. Croce et al., Nature 280:488–489 (1980)]. There is no evidence that murine retroviruses are pathogenic in man but these are able to infect human cells in tissue cultures. Obviously prior to human administration, monoclonal antibodies produced by mouse-human hybridomas must be documented to be free of any viral particles. Purification can be easily achieved by immunoadsorbance techniques or other chromatographic techniques known in the art.

2.2. Tetanus 2.2.1. Tetanus Toxin

Tetanus toxin, a neurotoxin produced by *Clostridium tetani*, has a molecular weight of approximately 150,000 daltons and consists of two polypeptide chains linked by a disulfide bond. With reduction, the extracellular form of the toxin is split into its constituent heavy and light chains. Papain digestion cleaves the molecule into a 47,000 dalton molecular weight fragment C and an approximately 95,000 dalton molecular weight fragment B [Helting and Zwisler, J. Biol. Chem. 252:187–193 (1977)]. Fragment C consists of the carboxy terminal half of the heavy chain and is responsible for the binding of the toxin to its in vivo receptor. Fragment B consists of the remaining portion of the heavy chain linked to the entire light chain. Although the function of fragment B is unknown, it is hypothesized to contain the toxic principle of the molecule.

2.2.2. The Disease

Tetanus is a serious infectious disease caused by the soil bacterium *Clostridium tetani*. The overall mortality rate of the disease is 45% to 55%, resulting in an estimated 50,000 deaths per year throughout the world [R. J. Rothstein and F. J. Baker II, J. Amer. Med. Assoc. 240(7): 675–676 (1978)]. Tetanus is associated with wounding. Any break in the skin, whether a deep puncture or superficial scratch, is susceptible to infection, particularly where unsanitary conditions prevail. Clostridial spores enter the wound; if the surrounding tissue environment is sufficiently anaerobic, the spores convert to the vegetative form of the gram-positive bacillus which produces a neurotoxin. The usual incubation period is between 7 and 21 days. Even in minute quantities, the potent neurotoxin has profound effects on the central nervous system and skeletal muscles.

Tetanus toxin acts on the skeletal muscle motor end plate, the brain, the sympathetic nervous system, and the spinal cord. It is specifically bound by the gangliosides of nerve tissue and the site of binding appears to be the synaptic membrane of nerve endings [W. E. van Heyningen, Tetanus, in: F. M. Burnet (editor), Immunology, Readings from Scientific American, W. H. Freeman and Co., San Francisco (1975)]. The binding leads to dysfunction of polysynaptic reflexes, producing the unopposed contraction of muscles with loss of antagonistic muscle function. This state is one of spastic paralysis; a victim of tetanus is unable to move even though the muscles of the body are contracting at full force. A classic early symptom of the disease is trismus, or lockjaw. Binding of tetanus toxin to cerebral gangliosides can cause seizures. Effects of the toxin on the sympathetic nervous system include extensive sweating, labile blood pressure and tachycardia.

2.2.3. Approaches to Prevention and Therapy

Tetanus can be prevented completely if the infected individual has been preimmunized against the toxin. Preimmunization consists of the sequential administration of tetanus toxoid (a non-toxic but immunogenic form of the neurotoxin produced by heat denaturation or formaldehyde treatment). The toxoid stimulates antibody production rendering the individual immune to the disease. However, not all individuals who may encounter infection by *Clostridium tetani* have been immunized, be it for socioeconomic, cultural or other reasons. Even individuals that have been preimmunized may no longer be immune to tetanus infection due to the decrease in circulating antibody titers over time after inoculation.

Another approach to tetanus prophylaxis is through passive immunization. If infection has occurred or is suspected, the onset of tetanus can be prevented by the administration of immunoglobulins against tetanus toxin. Conventional antiserum can be made on a large scale by hyperimmunizing horses with repeated large doses of tetanus toxoid and then refining their blood serum for human administration, an approach that has been taken to produce antisera against diphtheria, botulinum and gas gangrene toxins. A major disadvantage of equine anti-toxin antibodies is that their use can result in serum sickness, an allergic reaction to foreign (horse) proteins in the serum which can sometimes be fatal. For this reason, horse antisera are no longer prevalently in use, although they are still used occasionally during periods of outbreak of the diseases. Anti-tetanus antitoxin is presently available as human tetanus immunoglobulin—a polyclonal mixture of antibodies raised by conventional techniques. However, human antitoxins have not replaced all animal antitoxins because of the difficulty and expense of their production.

While the risk of serum sickness is reduced by using human polyclonal antibodies, there are other inherent problems, in addition to expense, associated with their use. Human antisera exhibit lot-to-lot variation, a problem compounded by the need to standardize each lot according to accepted government standards. There is always the danger in using a human blood (serum) product of transferring contaminants and disease-causing agents, e.g., hepatitis B virus. Another problem inherent in the use of human antisera is the need to immunize humans to prepare the immunioglobulins. This restricts the number of immunogens that may be used to those that are benign. In the case of backterial toxins for which no toxoid vaccine exists or for which toxin administrattion to humans is not benign, only humans recovering from the particular infection can serve as a source of human antisera; supply of such antisera is limited (see Section 3.1.2.1.).

Treatment of tetanus once it has been diagnosed can be a difficult and expensive procedure. Antibiotics effective against gram-positive bacilli, e.g., pencillin G, are administered to control the proliferation of the causative microoganism. Antitoxin is injected to bind and neutralize any remaining circulating neurotoxin and any toxin that continues to be produced. To help alleviate the severe neuromuscular disorders associated with the disease, anticonvulsants such as barbiturates (e.g., phenobarbital, amobarbital or thiopental) or diazepam are administered. Anticonvulsants are more effective than muscle relaxants such as mephenesin or methocarbamol; however, care must be taken to keep doses of anticonvulsants below the level that can cause postictal depression. In severe cases of tetanus, curariform compounds, like D-tubocurarine, which act as neuromuscular blocking agents, are given to the patient. These agents surpass the centrally acting drugs in the control of tetanic spasms but their use necessitates mechanical respiratory assistance. If the patient can be kept alive for a sufficiently long time, the effect of the toxin diminishes completely and the patient is restored to health.

2.3. Diphtheria

2.3.1. Diphtheria Toxin

Diphtheria toxin is produced by strains of *Corynebacterium diphtheriae* that are lysogenic for $\beta$-prophage, a bacteriophage which carries the structural gene for the toxin molecule. Diphtheria toxin is secreted by *C. diphtheriae* as a single polypeptide chain with a molecular weight of approximately 60,000 daltons. Its activity as an inhibitor of protein synthesis in mammalian cells is dependent upon an activating cleavage of a bond fourteen residues from the N-terminus of the molecule. Upon reduction of its cystine S—S bonds with thiol and exposure to trypsin, the activated toxin can be separated into an N-terminal fragment A (masked in the intact toxin) (MW approximately 21,150 daltons) and a fragment B (MW approximately 39,000 daltons). Fragment A is a stable, extremely potent enzyme with ADP-ribosylating activity capable of inactivating one of the elongation factors involved in protein synthesis. Fragment B is specific for receptors on sensitive cells and facilities transport of fragment A across the cell membrane into the cytoplasm. Fragment A must be complexed to fragment B in order to enter sensitive cells [B. D. Davis et al., in: Microbiology (3rd edition), Harper & Row, New York, N.Y., pp. 588–589 (1980)].

2.3.2. The Disease

Diphtheria initially affects the human respiratory tract where lysogenic *C. diphtheriae* lodge on the mucocutaneous tissue of the throat. As the bacteria multiply they produce diphtheria toxin which causes necrosis of neighboring tissue cells, which in turn promotes further proliferation of the bacteria. Eventually the diphtheria pseudomembrane (comprising fibrin, bacteria and trapped leukocytes) which is characteristic of the disease forms on the tonsils or posterior pharanyx and may spread to the nasal passages or into the larynx and trachea. Laryngeal diphtheria can result in suffocation by obstruction of the airway. Neurologic and cardiac complications may also eventually occur. While the disease rarely occurs in areas of the world where children are immunized against the toxin early in life, diphtheria is still prevalent in other countries where mass immunization is not practiced.

2.3.3. Approaches to Prevention and Therapy

As with tetanus disease (see Section 2.2.3.), diphtheria can be prevented by pre-exposure immunization of humans with a non-toxic, immunogenic, formaldehyde-treated diphtheria toxoid. In the case of infants, primary immunization is achieved with two inoculations, a month apart, at about three to four months of age. Thereafter, several booster injections are given during childhood to ensure continued protection.

Where infection is suspected or has occurred in a non-immunized individual, or in a previously immunized individual who is no longer immune, it is critical that passive immunization therapy with diphtheria antitoxin be begun without delay. Antitoxin is ineffective for neutralizing diphtheria toxin once the toxin has penetrated sensitive cells. Hence, large intramuscular injections of horse antisera delivered immediately upon suspicion of diphtheria is a generally practiced method of treatment. Allergic sensitivity to horse serum proteins must nevertheless be assessed prior to administration of the antitoxin. Obviously this can delay treatment. Moreover, lack of immediate allergic reaction does not negate the possibility of long term adverse reaction, such as serum sickness, to the horse serum proteins. Use of horse antisera poses the same disadvantages discussed for tetanus antitoxin in Section 2.2.3.

3. SUMMARY OF THE INVENTION

Prior to the present invention, it is Applicants' belief that there has been no report of a protective human monoclonal antibody against tetanus toxin or diphtheria toxin or even against any other bacterial toxin. Because the monoclonal antibodies of this invention can neutralize tetanus toxin or diphtheria toxin, they represent an example of new passive immunoprophylactic and immunotherapeutic agents with which to combat in vivo serious and potentially fatal diseases. The human monoclonal antibodies of this invention can be used to separate bacterial toxins from biological samples by forming antibody-toxin complexes which are separable from the remainder of the sample. The complexes can be further dissociated to yield purified toxin. Thus, these human monoclonal antibodies against bacterial toxins also represent useful reagents for the production and purification of vaccines and for clinical diagnosis.

The present invention provides a method for producing human monoclonal antibodies against bacterial toxins, including tetanus toxin and diphtheria toxin, by fusing readily accessible human peripheral blood lymphocytes with murine myeloma cell lines deficient in murine antibody production. The human monoclonal antibodies synthesized by these fused cell hybrids can be administered in a solution to infected (or potentially infected) individuals to prevent the onset of toxin-induced disease, such as tetanus and diphtheria, and to individuals showing symptoms of toxin-induced disease to treat the disease. The invention encompasses the extension of the human-rodent hybridoma technique to the production of human monoclonal antibodies against other icrobial toxins including, but not limited to, the exotoxins listed in Table I (besides tetanus toxin and diphtheria toxin) and the endotoxins (lipopolysaccharides) of Gram negative bacteria.

TABLE I

| BACTERIAL EXOTOXINS | |
|---|---|
| Organism | Toxin |
| *Clostridium tetani* | Tetanus toxin |
| *Corynebacterium diphtheria* | Diphtheria toxin |
| *Clostridium difficile* | *C. difficile* toxin |
| *Clostridium botulinum* | Botulism toxin |
| *Staphylococcus aureus* | *S. aureus* toxin |
| *Pseudomonas aeruginosa* | Exotoxin A |
| *Clostridium perfringens* | *C. perfringens* toxin |
| *Escherichia coli* | Enterotoxin |
| *Vibrio cholerae* | Cholera toxin |
| *Bacillus anthracis* | Anthrax toxin |
| *Clostridium welchii* | Gas gangrene toxin |
| *Shigella dysenteria* | Dysentery toxin |
| *Yersiniae pestis* | *Y. pestis* toxin |

Because the human monoclonal antibodies against bacterial toxins, specifically exemplified by tetanus toxin and diphtheria toxin, are produced by hybridoma techniques, the present invention provides theoretically immortal cell lines capable of consistently and inexpensively producing high titers of single specific antibodies against tetanus toxin or diphtheria toxin. This is a distinct advantage over the traditional technique of raising antibodies in immunized humans and animals where the resulting sera contain multiple antibodies of different specificities that vary in both type and titer with each animal and, in individual animals, with each immunization. Furthermore, animal sera require extensive purification to remove contaminants that can cause serum shock upon administration to humans; such procedures can add to the cost of traditional polyclonal antibodies. Even when human antisera are used, there may still be the problem of serum contaminants or inadequate supply.

The human monoclonal antibodies of this invention and the human-murine hybridomas that produce them offer several advantages over other monoclonal antibodies made by different monoclonal techniques. For example, the fused hybrids used herein are considerably more stable in cell culture and produce more antibody than virally transformed antibody-producing human lymphoblastoid cell lines which can die out over time in vitro. Moreover, because the myelomas used for cell fusion in this invention are murine in origin, there is the potential that the resulting hybridomas can be propagated in mice (in vivo) and human monoclonal antibodies so produced can be harvested in ascites fluid. This is in direct contrast to hybridomas made by fusing human lymphocytes with human myeloma cells or lymphoma cells. These human-human hybrids cannot be propagated in mice and must be cultured in vitro. Thus, the human-murine hybridomas offer greater flexibility in terms of cell line maintenance and antibody production. In addition, human-murine hybridomas obviate the potential problem of oncogenic viruses that may exist in human myeloma cells and may contaminate human-human hybridomas and their products. Finally, as in the case of human antisera versus animal antisera, the human monoclonal antibodies of this invention offer an advantage over murine monoclonal antibodies. By administering human immunoglobulins, the risk of serum sickness, anaphylactic shock or other allergic reaction in recipient individuals is considerably lowered, if not eliminated entirely.

The immortalized hybridoma cell lines of this invention further provide a source of genetic material potentially applicable to recombinant DNA technology. For instance, the mRNA of the hybridomas can be used to produce cDNA suitable for cloning into microorganism hosts such that antibodies may eventually be produced in microbial systems.

4. DESCRIPTION OF THE INVENTION

4.1. The Antigen

Heat denaturation or formaldehyde treatment of toxins produced by infections microorgansims, such as *Clostridium tetani* (tetanus toxin), *Corynebacterium diphtheriae* (diphtheria toxin), and others, yields toxoids compounds which retain their immunogenicity but are unable to elicit a disease response. Depending on the antibody desired, any of these toxoids is a suitable antigen with which to immunize peripheral blood lymphocyte donors or reactivate or immunize (that is, stimulate antibody production by) peripheral blood lymphocytes in vitro. Alternatively, non-toxic yet immunogenic fragments of toxins, mutant forms of toxins, or nonlethal doses of toxins can be used to immunize individuals or cells in virto. Any of the toxins listed in Table I (Section 3.) may serve as a source of immunogen. Antigens are administered intramuscularly or subcutaneously to individuals.

4.2. Somatic Cells

Human somatic cells capable of producing anitbody, specifically B lymphocyres, are suitable for fusion with myeloma cell lines. While B lymphocytes from biopsied spleens or lymph nodes of immunized individuals may be used, the more easily accessible peripheral blood B lymphocytes are preferred. If blood is chosen as the source of B cells (spleen, lymph nodes and tonsils are also sources), it is optimal that the blood be taken from individuals at the proper interval after a booster immunization (typically between 5 and 10 days after immunization). This is because activated antigen-specific antibody-producing B cells and their precursors are present in relatively high proportions in the circulating peripheral blood pool for only a brief time following immunization of the individual with a particular antigen. It is important, if not crucial, to appreciate this transiency so as to harvest peripheral blood at the time when the number of desired recently-activated postimmunization antibody-producing lymphocytes is at or near maximum: the greater the number of desirable fusible B lymphocytes, the greater the likelihood of obtaining the desired antibody-secreting hybridoma.

After this time period, the lymphocytes may circulate in smaller numbers in certain individuals for a finite period of time. It may prove possible to reactivate these lymphocytes in vitro to serve as fusion partners. This reactivation process is also known as in vitro lymphocyte stimulation. Lymphocytes from humans recovering from toxin-induced disease or sensitized through natural exposure to toxin antigens may also prove suitable as fusion partners directly or after in vitro stimulation.

It is also preferable but not absolutely obligatory (See Section 5.1.3.) to enrich peripheral blood samples for B lymphocytes, that is, to remove other mononuclear cells such as T lymphocytes from the preparation ultimately used for fusion. Again, this enrichment measure (which may be performed by such techniques as Ficoll-Hypague density gradient centrifugation after rosetting or cell sorting) increases the probability of obtaining the desired hybridoma cell line.

4.3 Myeloma Cells

Specialized myeloma cell lines possessing characteristics that make them most suitable for hybridoma formation have been developed from lymphocyte tumors [G. Köhler and C. Milstein, Europ. J. Immunol. 6:511-519 (1976); M. Shulman et al., Nature 276:269-270 (1978)]. To facilitate the selection of fused hybridomas among unfused and similarly indefinitely self-propagating myeloma cells, mutant myeloma lines are used. These myeloma cells generally have enzyme or other deficienies which render them incapable of growing in certain selective media that do support the growth of hybridomas. Myeloma lines have also been developed to eliminate the problem arising from the inherent ability of lymphocyte tumor cells to produce their own antibodies. It is the objective of hybridoma technology to produce homogeneous monoclonal antibody under the control of genes contributed by the somatic cell component of the fused hybrid. Consequently, myeloma cell lines incapable of producing light or heavy immuoglobulin chains or those deficient in antibody secretion mechanisms are used. Finally, myelomas demonstrating high fusion efficiency are preferred.

Several mouse myeloma cell lines may be used for the production of fused cell hybrids, including X63-Ag8, NS1-Ag4/1, MPC11-45.6TG1.7, SP2/O-Ag14, FO, S194/5XXO.BU.1 and, as in the example of the present invention, P3X63-Ag8.653. [G.J. Hammerling, U. Hammerling and J. F. Kearney (editors), Monoclonal antibodies and T-cell hybridomas, in: J.L. Turk (editor), Research Monographs in Immunology, Vol. 3, Elsevier/North Holland Biomedical Press, New York (1981)].

4.4. Fusion

Methods for generating hybrids of antibody-producing B lymphocytes and myeloma cells usually comprise mixing somatic cells with myeloma cells in about a 1:1 proportion (though the proportion may vary from about 20:1 to about 1:3, respectively) in the presence of an agent or agents (chemical or electrical) that promote the fusion of cell membranes. It is usually preferred that the same species of animal serve as the source of the somatic and myeloma cells used in the fusion procedure (though this is not the preferred approach of the present invention). This measure can enhance the number of stable hybrids obtained. It is a significant feature of this invention that stable hybridomas were produced from the fusion of human peripheral blood lymphocytes and mouse myeloma cells. The human monoclonal antibodies synthesized by the hybridomas of this invention are better suited for human use than the murine products of mouse-mouse hybridomas.

Fusion methods have been described by Köhler and Milstein [Nature 256:495-497 (1975) and Eur. J. Immunol. 6:511-519 (1976)], and by Gefter et al. [Somatic Cell Genet. 3:231-236 (1977)]. The fusion-promoting agent used by those investigators were Sendai virus and polyethylene glycol (PEG), respectively. The fusion procedure of the example of the present invention is a modification of the method of Gefter et al. [supra]; PEG is added to the mixture of human B lymphocytes and myeloma cells to promote the formation of fused cell hybrids.

4.5. Isolation of Clones and Antibody Detection

Fusion procedures usually produce viable hybrids at very low frequency, about $1 \times 10^{-6}$ to $1 \times 10^{-8}$. Because of the low frequency of obtaining viable hybrids, it is essential to have a means to select fused cell hybrids from the remaining unfused cells, particularly the unfused myeloma cells. A means of detecting the desired antibody-producing hybridomas among the other resulting fused cell hybrids is also necessary.

Generally, the fused cells are cultured in selective media, for instance HAT medium containing hypoxanthine, aminopterin and thymidine. HAT medium permits the proliferation of hybrid cells and prevents growth of unfused myeloma cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the media so that inhibited cells can synthesize purines using the nucleotide salvage pathway. The myeloma cells employed are mutants lacking hypoxanthine phosphoribosyl transferase (HPRT) and thus cannot utilize the salvage pathway. In the surviving hybrid, the B lymphocyte supplies genetic information for production of this enzyme. Since B lymphocytes themselves have a limited life span in culture (approximately two weeks), the only cells which can proliferate in HAT madia are hybrids formed from myeloma and spleen cells.

To facilitate screening of antibody secreted by the hybrids and to prevent individual hybrids from overgrowing others, the mixture of fused myeloma and B lymphocytes is cultured in HAT medium in multiple wells of microtiter plates. In two to three weeks, when hybrid clones become visible microscopicaly, the supernatant fluid of the individual wells containing hydrid clones is assayed for specific antibody. The assay must be sensitive, simple and rapid. Assay techniques include radioimmunoassays, enzyme immunoassays, cytoxicity assays, and plaque assays.

Newly formed hybridomas are unstable because of their polyploid chromosomal number. Chrommomsomes are shed with each subsequent cell division until a more stable chromosomal number is reached. As many as 50% of hybridomas lose the property of antibody secretion due to this rapid shedding of chromosomal material. Hybrids not producing antibody will tend to grow faster in tissue culture and may overgrow antibody producers. To prevent overgrowth and to select a stable rapidly dividing clone that secretes large amounts of antibody, the hybrids are cloned.

To insure that the progeny of only a single cell is being grown, the hybrid is cloned either by selecting a single cell by micromanipulation or by culturing the cells at limiting dilution in microtiter plates or in soft agar. The cells are seeded at limiting concentration such that there is statistical certainty that the clone arising in a well was derived from only a single progenitor. The subclones are rescreened for antibody. The hybrid cells are then grown in bulk culture to produce large amounts of antibody in vitro and can be harvested by decantation, filtration, or centrifugation. To generate even greater antibody amounts, the hybridoma cells are injected into the peritoneal cavity of a mouse or other animal, e.g., a rat, to produce tumor ascites which contain antibody at 5-50 mg/ml, up to a thousand-fold higher concentration than produced in vitro. Besides ascites fluid, the animals' sera can also be tapped to provide monoclonal antibodies in high concentration. The hybrid cells can be stored indefinitely in liquid nitrogen.

The number of antibody-producing clones may be increased by pre-selecting potential donor B lymphocytes to enrich for those of desired specificity or by plating only antibody-producing hybrids. These techniques make monoclonal antibody production more efficient and less labor intensive. Anywhere from 1 to 30% of the hybridomas obtained produce the desired antibody.

4.6. Uses for Bacterial Toxin Specific Human Monoclonal Antibodies

Human monoclonal antibodies specific to bacterial toxins can be used clinically for the prevention or treatment of disease. The mode of administration of the monoclonal antibodies varies depending on the site of the toxin. For example, for toxins such as tetanus which act systemically, the antibodies can be administered parenterally; for toxins such as that produced by *Clostridium difficile* which act in the gastrointestinal tract, the antibodies can be administered orally. The monoclonal antibodies may be suspended or dissolved in any of several suitable liquid vehicles, e.g., a saline solution, and delivered to the individual by injection or orally in a stable form. As a preventative measure, administration of the antibody composition may occur immediately after infection occurs (or is suspected) and before the onset of any noticeable symptoms. When symptoms of disease are observed, the human monoclonals can be delivered alone or in conjunction with other chemotherapeutic agents used to treat the disease.

Other applications for toxin-specific monoclonal antibodies are in affinity chromatography systems for the purification of toxins or toxoids, as in vaccine production, for example. The monoclonal antibodies also can be used to detect or quantify with great accuracy the presence of toxins at sites of infection or in body fluids and tissue.

5. EXAMPLES

5.I Construction of Hybridomas Secreting Monoclonal Antibodies to Tetanus Toxin and Diphtheria Toxin

5.1.1. Immunization with Toxoid

In two separate series of experiments in which human monoclonal anitbody-secreting mouse-human hybridomas were constructed, volunteers were immunized with tetanus and diphtheria toxoids absorbed (for adult use) (Wyeth Laboratories, Marietta, Pa.). Peripheral blood was obtained from the volunteers 6-7 days post-immunization which corresponds to the time of peak in vivo circulation of cells that spontaneously produce anti-tetanus toxoid and anti-diphteria toxoid antibody. No volunteer had received a tetanus and diphtheria vaccination within the preceding two years.

5.1.2. Isolation of Mononuclear Cells

The collected blood (approximately 50µl) was treated with heparin to prevent coagulation of the various blood cells, diluted with balanced salt solution, and subjected to Ficoll-Hypaque density gradient centrifugation to separate the mononuclear cells in the blood from red blood cells and granulocytes. [Boyum, Scand. J. Clin. Lab. Invest. Suppl. 97, 21:77-88 (1968)].

5.1.3. Enrichment for B Lymphocytes

The mononuclear cells were washed and then next incubated with 2-aminoethylisothiuronium bromide hydrobromide (AET)treated sheep red blood cells (SRBC), which causes the formation of T lymphocyte rosettes, and allows for the removal of T lymphocytes from the suspension.

The red blood cells were prepared by incubation with 0.14M AET (1:4 ratio of cells: AET) for 20 minutes at 37° C. with occasional stirring, followed by four washes with PBS. The mononuclear cell suspension ($10^7$ ml) was then incubated with an equal volume of 1% AET-treated sheep red blood cells in heat-inactivated and SRBC-adsorbed fetal calf serum (FCS) for 5 minutes at 37° C. The mixture was centrifuged at 200xg for 5 minutes and incubated again at 4° C. for 1 hr. The pellet was gently resuspended making sure to disperse all clumps layered over Ficoll-Hypaque, and centrifuged at 60xg for 10 minutes and then 400xg for 25 minutes. The cells at the interface (B lymphocyte-enriched mononuclear cells) were collected and washed with RPMI 1640 [A. Saxon et al., J. Immunol. Methods. 12:285–288 (1976)]. The pellet which contains T lymphocytes rosetting with the erythrocytes may be discarded.

In the second series of experiments, the enriched B cells from the three volunteers were pooled prior to fusion. In addition, blood was obtained from a fourth volunteer after the same immunization procedure and his whole mononuclear cell fraction was used for fusion without enriching for B cells as just described.

5.1.4. Fusion Procedure for Hybrid Formation

The enriched B lymphocytes were fused with an equal number of P3-X63-Ag 8.653 mouse myeloma cells, using a standard fusion protocol such as the following: equal numbers of myeloma cells and enriched B lymphocytes were mixed in a centrifuge tube, topped with saline and centrifuged at 200xg for 10 minutes. The supernatant was discarded and the pellet disrupted by gently tapping the tube. The pellet was resuspended in 1.0 ml of 50% (v/v) polyethylene glycol (PEG) 6000 (Fisher Scientific Co., Fairlawn, N.J.), a fusing agent. The cells were incubated for 1 minute in this solution with constant shaking of the tube and then incubated in a 37° C. bath for 90 seconds, with constant swirling of the suspension. The fusion reaction was stopped by the slow addition of 20 ml saline; 1 ml was added over the first 30 seconds, 3 ml over the next 30 seconds with the remainder added during the next 1 minute. The tube was then topped with saline and allowed to stand for 5 minutes. The cell suspension was centrifuged at 200xg for 10 minutes, the supernatant discarded, the pellet washed with standard medium, and centrifuged again.

After removal of the supernatant, the cells were resuspended in HAT medium (RPMI 1640 medium containing 15% fetal calf serum, $2 \times 10^{-3}$M glutamine, $1 \times 10^{-3}$ M sodium pyruvate, 100 µg/ml gentamycin, 100 units/ml penicillin $1 \times 10^{-4}$ M hypoxanthine, $1.6 \times 10^{-5}$ M thymidine (Gibco, Grand Island, N.Y.), $4 \times 10^{-7}$M aminopterin (Sigma Chemical Co., St. Louis, Mo.), $5 \times 10^{-5}$M 2-mercaptoethanol (Eastman Kodak, Rochester, N.Y.), 5–10 µg/ml insulin and 5–10 µg/ml transferrin (Collaborative Research, Lexington, Mass.) and seeded at a density of $1.5 \times 10^5$ cells/0.2 ml ($7.5 \times 10^5$/ml) in microtiter wells (Costar 3596, Costar Data Packaging, Cambridge, MA) containing $3 \times 10^3$ irradiated mouse peritoneal macrophages as a feeder layer. In the instance where the mononuclear cell fraction had not been enriched for B cells, the same fusion protocol was used except that the fusion cells were seeded at a density of $1.5 \times 10^6$ cells/0.2 ml. Culturing in HAT medium allows growth of hybrid cells while preventing growth of unfused myeloma cells and thus plays a role in selecting for hybrids and preventing overgrowth by non-fused myeloma cells.

5.1.5. Screening for Anitbody Producing Hybrids

After approximately 3 weeks in culture, hybrid cell colonies were observed in the microtiter wells. To screen for those hybrids secreting anti-tetanus toxoid or anti-diphtheria toxoid antibodies, the supernatants were removed from the wells and subjected to an enzyme-linked immunoadsorbent assay (ELISA) [see Engvall and Perlman, Immunochem. 8: 871–876 (1971); R.A. Insel et al., J. Infect. Dis. 144(6):521–529 (1981); and F. Gigliotti and R.A. Insel, J. Clin. Invest. 70:1306–1309 (1982)].

For example, in the ELISA assay for anti-tetanus toxin antibody, 100 µl of purified tetanus toxoid (Mass. Public Health Laboratories, Boston, Mass.) at a concentration of 10 µg/ml was incubated in microtiter plates for 90 minutes at 37° C. (Microbiological Associates, Walkersville, MD) to produce binding of antigen to the plates. The plates were washed with PBS and 0.05% Tween 20 (PBS-T) to remove unbound antigen. Supernatants from wells containing hybrids were then added to these plates and incubated overnight to allow binding of any anti-tetanus antibodies in the supernatants to the purified antigen.

Detection of this antibody-antigen reaction was accomplished by the use of alkaline phosphatase-labelled antisera specific for human IgG, IgA, and IgM (Atlantic Antibodies, Scarborough, Me.) [Insel et al. (1981), supra. Alkaline phosphatase-conjugated class-specific antibodies to human immunoglobulins were diluted in PBS-T, added to the microtiter plates containing tetanus antigen and hybrid supernatant and incubated for at least 3 hours. The anti-immunoglobulin binds to tetanus antibody-antigen complexes. Unattached enzyme-linked anti-immunoglobulin is washed off the plate. To detect the binding of the anti-immunoglobulin and so the presence of anti-tetanus antibody in the supernatants, a suitable substrate for the enzyme such as p-nitrophenol was added to the plates in a diethanolamine buffer at pH 9.8 and the plates were incubated for 1 hr. at 22° C. Sodium hydroxide (NaOH) was added to a concentration of 0.6M to stop the alkaline phosphatase-substrate reaction. Since this reaction causes a color change, the reaction was detected by a spectrophotometric optical density reading at 400 nm. Control plates (i.e., containing no antigen or no supernatant) were similarly read to provide a background measure of optical density. ELISA assays were also performed with diphtheria toxoid (Massachusetts Public Health Biologic Laboratories, Boston, MA), at 1 µg/ml.

5.1.6. Cloning of Anti-Tetanus Toxin and Anti-Diphtheria Toxin Anti-Body-Producing Hybrids Once those hybrids producing the tetanus antibody were identified, they were selectively cultured and cloned. In the fusion in the first series of experiments from which a stable clone producing protective human monoclonal anit-tetanus toxin antibodies ("clone 9F12") was derived, $6 \times 10^6$ B lymphocytes were initially seeded into 80 microtiter wells. Hybrids were observed in 28 of the 80 wells by 3 weeks after fustion. Five of the 28 wells contained human anit-tetanus toxoid antibody, all of the IgB isotype. Four of the 5 wells were passed at 10 cells/well (in a microtiter dish containing a mouse macrophage feeder layer) and reassayed for continued antibody production. Following five of these low density passages, hybrid clone 9F12 was cloned twice in a limiting dilution assay at one cell per well. After several cycles of this procedure, one clone, 9F12, continued to produce high titers of antibody of the IgG class with k light chain (see Section 5.2). No mouse immunoglobulin was detectable. Karyotyping performed after the second cloning by limiting dilution assay showed the cells to have a modal chromosomal number of 108 with approximately 101 mouse and 6–7 intact human chromosomes. After six months in culture antibody production was determined to be 5–10 µg/ml and antibody production continues at 19 months after fusion (see Section 5.2.).

Also in this first series of experiments, following the same protocol, B lymphocytes from 3 other immunized volunteers were fused and seeded into a total of 384 wells. Viable hybrids grew in 94 of the wells and 5 of these secreted human anti-tetanus toxoid antibody of the IgG isotype. Low density passage was attempted on 3 of the secreting hybrids but antibody production could not be maintained for longer than 1 month. Human anti-diphtheria toxoid antibody was detected in supernatants of 3 of the 122 hybrids. No supernatants reacted with both tetanus and diphtheria toxoids.

In the second series of experiments, hybrid cell growth was observed in 76% of the wells seeded with unfractionated mononuclear cells from the single volunteer and in 46% of the wells seeded with the pooled enriched B cell fraction from the three other volunteers. By day 18, sufficient growth for screening was present. Of the 73 wells with hybrids after fusion of unenriched mononuclear cells, nine (12%) were positive for antibody to diphtheria toxin or tetanus toxin. Antibody to diphtheria toxin or tetanus toxin was detected in 19 (14%) of the wells showing growth after fusion of the enriched B cell fraction. These data are presented in Table II. These data indicate that mouse-human hybrids were obtained in 205 (53%) of the microtiter wells initially seeded. Twenty-eight (14%) of these hybrid cell lines secreted antibody of predefined specificity for either diphtheria toxin or tetanus toxin.

TABLE II

RESULTS OF FUSING HUMAN PERIPHERAL BLOOD MONONUCLEAR CELLS OR AN ENRICHED B CELL FRACTION WITH MOUSE MYELOMA CELLS

|  | # wells seeded | # well with growth at 18 days | # wells positive for antibody to DT[1] or TT[2] |
|---|---|---|---|
| Mononuclear cells | 96 | 73 (76%)[3] | 9 (12%)[4] |
| Enriched B cell fraction | 288 | 132 (46%)[3] | 19 (14%)[4] |

[1]DT stands for diphtheria toxin
[2]TT stands for tetanus toxin
[3]Percent of seeded wells with hybrids
[4]Percent of wells with hybrids positive for specific antibody Antibody-secreting hydrids were passed at a density of 10 cells/well into 96 wells of a microtiter plate over a mouse peritoneal macrophage feeder layer until most of the subsequent colonies were positive for antibody production and appeared to be growing well in culture. At this point an attempt was made to stabilize antibody production in two of the mouse-human hybrids producing antibody directed to diphtheria toxin. On of these hydrids was successfully cloned by repeated (2–3) limiting dilution and has continued to produce antibody seven months after fusion.

Hybrids not initially passed at 10 cells/well were expanded and repeatedly passed as 1 ml cultures in 24 well tissue culture trays (Costar 3524). Although antibody production was lost by most of these hybrids, a few did contiue to secrete antibody after three weeks in continuous culture. We attempted to clone three of these hybrids that continued to secrete antibody. One of the three hybrids, which secretes antibody directed to tetanus toxin, was successfully cloned and also has continued to secrete antibody seven months after fusion. Therefore, by passage of the hybrids at 10 cells/well followed by cloning by limiting dilution we have been able to maintain antibody production in 40% (2/5) of the hybrids we have tried to stabilize. In general, we had little success in obtaining long-term antibody production when fewer than 25% of the colonies resulting from the first passage at 10 cells/well were positive for antibody.

5.2. Characterization of Hybrid Clones

The concentration of anitbody secreted by a hybrid clone into the tissue culture supernatant was determined by radial immunodiffusion using an LC-partigen IgG Kit (Calbiochem-Behring Corp., La Jolla, Ca.) and also by nephelomety, performed in the Clinical Immunilogy Laboratory of Strong Memorial Hospital, Rochester, N.Y.

To concentrate the antibody secreted by the clone ten-fold, the tissue culture supernatant of the clone was combined in a 1:1 ratio (v/v) with saturated ammonium sulfate (SAS), followed by dialysis against PBS. Characterization of the immunoglobulin heavy and light chain of the secreted antibody was accomplished by Ouchterlony immunodiffusion using goat anti-human and anti-mouse antisera (Cappel Laboratories, Cochranville, Pa.).

5.3. Determination of Anit-Tetanus Toxin Monoclonal Antibody Specificity

In order to determine to which part of the tetanus toxin the antibody of a particular hybrid binds, the toxin was first labeled with [$^{125}$I]iodide, cleaved with papain into two distinct fragments (B and C), reacted with antibody concentrated from the hybrid tissue culture supernatant, precipitated the toxin-antibody complex, and analyzed by SDS-polyacrylamide gel electrophoresis and autoradiography.

5.3.1. Iodination of Tetanus Toxin

Purified tetanus toxin was radio-iodinated by the lactoperoxidase method at 22° C. for 25 minutes [J. J. Marchalonis, Biochem. J. 113:299–305 (1969)]using Enzymobeads (Bio-Rad Laboratories, Richmond, CA).

5.3.2. Papain Cleavage of Tetanus Toxin

The iodinated toxin (1 mCi/mg) was incubated with papain (Boehringer Mannheim Biochemicals, Indianapolis, Ind.) at a concentration of 2 units papain/mg toxin for 3 hours at 55° C. This digestion resulted in cleavage of the toxin into two fragments: C, consisting of the carboxyl terminal half of the heavy chain, and B, consisting of the amino terminal portion of the heavy chain linked by a disulfide bond to the light chain of the toxin

[T. B. Helting and O. Zwisler, J. Biol. Chem. 252(1):187–193 (1977)].

5.3.3. Precipitation of Tetanus Toxin Fragment-Antibody Complexes

The papain digest was incubated with the antibody-containing hybrid supernatant concentrated with 10 SAS, as described in Section 2, for 1.5 hours at 4° C. The antigen-antibody complexes formed were precipitated with formalin-fixed *S. aureus* Strain Cowan 1 (Enzyme Center, Inc., Boston, Mass.), a bacterial strain whose cell wall protein binds to the antibody and causes the precipitation of such complexes. The precipitate was washed three times with PBS.

5.3.4. Identification of Antibody Specificity

The anitgen-antibody precipitates were solubilized by vortexing the pellet in SDS sample buffer [Laemmli, Nature (London) 227:680–685 (1970)]and incubating the suspension at 20° C. The sample was centrifuged and the supernatant boiled for 2 minutes prior to loading onto the gel in 5% 2-mercaptoethanol in order to reduce the disulfide linkages of the toxin-fragment (and of the antibody). The sample was then loaded onto a 7.5% SDS-polyacrylamide gel [Laemmli, supra]. The labelled toxin fragments (or chains) migrate in the gel according to size and can be identified by comparison to marker fragments (or chains) of known identity and size applied to parallel wells on the gel. Detection of the fragment was accomplished by autoradiography with Kodak X-Omat AR film.

5.4. Determination of Biological Activity of Anitbody Produced

The biological activity of antibody produced by fusion hybrids was determined by the mouse tetanus toxin neutralization assay. Purified tetanus toxin (Lot 39, Mass. Public Health Biologic Laboratories) in PBS with 0.2% gelatin (PBS-G) was diluted with an equal volume of either PBS-G, 10-fold saturated ammonium sulfate (SAS) concentrated mouse myeloma cell tissue culture supernatant (653), or 10-fold SAS concentrated human monoclonal antibody (9F12) and administered as a 0.5 ml subcutaneous injection to the right inguinal fold of 15 to 18 g female CD-1 (Charles River Laboratories, Wilmington, MA). Prior to injection, the toxin/antibody or toxin/control mixtures were incubated for 1–2 hours at 22° C. Neutralization of the toxin by the antibody from the hybrid culture resulted in survival of the injected mice, whereas the control animals were all killed or paralyzed by the toxin. (The minimal lethal dose of this toxin preparation, defined as 100% death by 96 hours, was 0.16 ng.) Data from a representative experiment from the first series of experiments are shown in Table III.

TABLE III

MOUSE TETANUS TOXIN NEUTRALIZATION ASSAY USING HUMAN MONOCLONAL ANTIBODY AS ANTITOXIN

| Toxin Dose | # Dead/# Total at Indicated Time (Hrs) after Toxin Adminstration | | | | | |
|---|---|---|---|---|---|---|
| | 24 | 48 | 72 | 96 | 120 | 144 |
| 0.16 ng in PBS-G* | 0/9 | 0/9 | 8/9 | 9/9 | — | — |
| 0.16 ng in 653* | 0/5 | 0/5 | 4/5 | 5/5 | — | — |
| 0.16 ng in 9F12ᵛ | 0/5 | 0/5 | 0/5 | 0/5 | 0/5 | 0/5 |
| 0.08 ng in PBS-G | 0/5 | 0/5 | 0/5 | 1/5 | 4/5 | 5/5 |
| 0.08 ng in 653 | 0/5 | 0/5 | 0/5 | 2/5 | 4/5 | 5/5 |
| 0.08 ng in 9F12 | 0/5 | 0/5 | 0/5 | 0/5 | 0/5 | 0/5 |
| 0.04 ng in PBS-G | 0/5 | 0/5 | 0/5 | 0/5 | 0/5 | 0/5 |
| 0.04 ng in 653 | 0/5 | 0/5 | 0/5 | 0/5 | 0/5 | 0/5 |
| 0.04 ng in 9F12 | 0/5 | 0/5 | 0/5 | 0/5 | 0/5 | 0/5 |

*All animals receiving 0.16 or 0.08 ng of toxin in PBS-G or 653 died by 6 days while those receiving 0.04 ng survived but had right-sided paralysis.
ᵛAll 3 groups receiving 9F12 showed no clinical signs of tetanus.

All 15 animals that received tetanus toxin neutralized by preincubation with antibody 9F12 were completely protected. On the other hand, all 34 animals that received toxin preincubated with phosphate buffered saline-0.2% gelatin, or the parent mouse myeloma cell culture supernatant, were either killed or paralyzed by the toxin. These results were reproducible in four replicate determinations. To the best of out knowledge this is the first demonstration of toxin neutralization by a human monoclonal antibody [F. Gigliotti and R.A. Insel, J. Clin. Invest. 70:1306–1309 (1982)].

Hybridoma antibody 9F12 binds both intact tetanus toxin and toxin fragment B. Serum (FG) from the individual whose lymphocytes were used in the fusion producing 9F12 bound both fragments B and C as well as the intact toxin. Other experiments demonstrated that 9F12, in contrast to the FG serum, is unable to bind purified toxin heavy or light chains that were obtained by treatment of tetanus toxin with dithiothreitol and urea and isolation of the chains by gel filtration as described. This would suggest that the antigenic specificity of 9F12 is directed to either a conformational epitope requiring the disulfide linkage of the heavy and light chain or an epitope on one of the chains that was denatured with reduction and dissociation of the toxin.

The ability of the monoclonal antibody directed to diphtheria toxin, to neutralize the native toxin was tested in dthe second series of experiments by incubating serial dilutions of the anitbody (prepared by ammonium sulfate precipitation of tissue culture supernatant) with an equal volume of diphtheria toxin prepared for Schick testing (Massachusetts Public Health Biologic Laboratories, Boston, MA). PBS - 0.2% gelatin was used as the diluent and negative control. After incubation for one hour at room temperature, 0.1 ml was injected 30 intradermally into a non-immune New Zealand White rabbit (Dla:(NZW)SPF Hazleton Dutchland Inc., Denver, PA). The injection sites were examined daily for four days for erythema and necrosis of the skin.

In this assay of diphtheria toxin activity, monoclonal antibody of cell line 16M3F10, directed to diphtheria toxin, at concentrations of 6 μg/ml or greater completely neutralized the toxin. Further four-fold dilutions of the antibody only partially neutralized the toxin.

Table IV summarizes the characteristics of the 3 cloned mouse-human hybrid cells lines. Combining the results of both series of experiments, hybrids grew in 327 of 848 wells seeded (38.5%) and 41 (12.5%) of these hybrids secreted antibody of predefined specificity for diphtheria toxin or tetanus toxin. From these 41 hybrids, 3 (30%) of 10 hybrids cloned continue to produce human monoclonal antibody in long term culture. Table IV indicates that cloning efficiency and the amount of antibody produced in tissue culture are consistent with what would be expected from intraspecies mouse-mouse fusions [J. W. Godin, J. Immunol. Methods 39:285–308 (1980).

TABLE IV
SUMMARY OF CLONED MOUSE-HUMAN HYBRID CELL LINES

| Line | Binding Specificity | Antibody Class | Tissue Culture Antibody Levels (μg/ml) | Duration of Antibody Production in Culture | Protection in Animal Model |
|---|---|---|---|---|---|
| 9F12 | Tetanus toxin | IgG | 5.3 | 19 mo | Yes |
| 16M3C9 | Tetanus toxoid | IgG | 1.6 | 7 mo | N.T.[1] |
| 16M3F10 | Diphtheria toxin | IgG | 5.3 | 7 mo | Yes |

It is apparent that many modifications and variations of this invention as hereinbefore set forth may be made without departing from the spirit and scope thereof. The specific embodiments described are given by way of example only and the invention is limited only by the terms of the appended claims.

Two cell lines, 9F12 and 16M3F10 as described herein have been deposited with the American Type Culture Collection, Rockville, Maryland, and have been assigned accession numbers ATCC Nos. HB8177 and HB8363 respectively. The invention described and claimed herein is not to be limited in scope by the cell lines deposited, since the deposited embodiments are intended as two illustrations of one aspect of the invention and any equivalent cell lines which produce functionally equivalent monoclonal antibodies are within the scope of this invention. Indeed, various modifications of the invention in addition to those shown and described herein will become apparent to those skilled in the art from the foregoing description. Such modifications are also intended to fall within the scope of the appended claims.

We claim:

1. A continuous cell line which produces human anti-exotixin antibodies, comprising: a stable fused cell hybrid of a human peripheral blood lymphocyte immunized by a toxin, or an imunogenic fragment thereof, or a toxoid prepared from an exotoxin, or an immunogenic fragment thereof, and a mouse myeloma cell, in which the antibodies are capable of neutralizing exotoxin.

2. A continuous cell line which produces human anti-endotoxin antibodies, comprising: a stable fused cell hybrid of a human peripheral blood lymphocyte immunized by a toxin, or an imunogenic fragment thereof, or a toxoid prepared from an endotoxin, or an immunogenic fragment thereof, and a mouse myeloma cell, in which the antibodies are capable of neutralizing endotoxin.

3. A continuous cell line which produces human anit-tetanus toxin antibodies, comprising: a stable fused cell hybrid of a tetanus toxin-immunized or toxoid-immunized human peripheral blood lymphocyte and a mouse myeloma cell, in which the anitbodies are capable of neutralizing tetanus toxin.

4. A continuous cell line which produces human anti-diphtherial toxin antibodies, comprising: a stable fused cell hybrid of a diphtheria toxin-immunized or toxoid-immunized human peripheral blood lymphocyte and a mouse myeloma cell, in which the antibodies are capable of neutralizing diphtheria toxin.

5. A continuous cell line which produces human anti-exotoxin antibodies, comprising: a stable fused cell hybrid of a human peripheral blood lymphocyte obtained from an individual and subsequently stimulate in vitro with a bacterial exotoxin, or an immunogenic fragment thereof, or and exotoxoid, or an immunogenic fragment thereof, and a mouse myeloma cell, in which the anitbodies are capable of neutralizing exotoxin.

6. A continuous cell line which produces human anti-endotoxin antibodies, comprising: a stable fused cell hybrid of a human peripheral blood lymphocyte obtained from an individual and subsequently stimulated in vitro with a bacterial endotoxin, or an immunogenic fragment thereof, or an endotoxoid, or an immunogenic fragment thereof, and a mouse myeloma cell, in which the anitbodies are capable of neutralizing endotoxin.

7. A continuous cell line which produces human anit-tetanus toxin antibodies, comprising: a stable fused cell hybrid of a human peripheral blood lymphocyte stimulated in vitro with tetanus toxin, or an immunogenic fragment thereof, or tetanus toxoid, or an immunogenic fragment thereof, and a mouse myeloma cell, in which the antibodies are capable of neutralizing tetanus toxin.

8. A continuous cell line which produces human anti-diphtheria toxin antibodies, comprising: a stable fused cell hybrid of a human peripheral blood lymphocyte stimulated in vitro with diphtheria toxin, or an immunogenic fragment thereof, or diphtheria toxoid or an immunogenic fragment thereof and a mouse myeloma cell, in which the antibodies are capable of neutralzing diphtheria toxin.

9. Cell line 9F12.

10. Cell line 16M3F10.

* * * * *